(12) United States Patent
Ishikawa et al.

(10) Patent No.: US 6,398,710 B1
(45) Date of Patent: Jun. 4, 2002

(54) RADIATION DOSIMETRY SYSTEM

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/478,591

(22) Filed: Jan. 6, 2000

Related U.S. Application Data (60) Provisional application No. 60/115,192, filed on Jan. 6, 1999.

(51) Int. Cl.[7] .......................... A61N 5/00; H05B 33/00; A61B 5/00
(52) U.S. Cl. .................. 600/3; 250/484.5; 600/300
(58) Field of Search .................. 600/317, 300–436, 600/1–3; 601/3; 250/484.5; 345/349; 424/1.49; 378/65

(56) References Cited

U.S. PATENT DOCUMENTS

| | | | |
|---|---|---|---|
| 4,976,266 A | | 12/1990 | Huffman et al. ............. 128/659 |
| 4,999,504 A | * | 3/1991 | Braunlich et al. ........ 250/484.5 |
| 5,273,738 A | * | 12/1993 | Matthews et al. .......... 424/1.49 |
| 5,620,479 A | * | 4/1997 | Diederich ....................... 601/3 |
| 5,621,779 A | * | 4/1997 | Hughes et al. ................. 378/65 |
| 5,704,352 A | | 1/1998 | Tremblay et al. ............ 128/630 |
| 5,704,890 A | | 1/1998 | Bliss et al. ..................... 600/1 |
| 5,833,603 A | | 11/1998 | Kovacs et al. .............. 128/620 |
| 6,222,544 B1 | * | 4/2001 | Tarr et al. .................... 345/349 |

OTHER PUBLICATIONS

Gratz, et al. "Smart Card for Detection of Alpha Radiation" Seniors and Actuators A. Ch. Elsevier Sequoia S.A., Lausanne, vol. 60, No. 1–3, pp. 431–435, May 1, 1997.

\* cited by examiner

*Primary Examiner*—John P. Lacyk
*Assistant Examiner*—Nikita R. Veniaminov
(74) *Attorney, Agent, or Firm*—Howison, Thoma & Arnott, L.L.P.

(57) ABSTRACT

A radiation dosimetry system (110) using miniature implanted transponder balls. A patient having a tumor that is the target of the radiation treatment lies in a treatment area with the tumor positioned beneath a target (112) used for alignment purposes. The system (110) is controlled and monitored by a CPU (114) which receives instructions from a radiologist operating a control panel (116), and displays control parameters, data and graphics to the radiologist on a display (118). The CPU (114) controls an RF system operating through a broad-band antenna (120) and directed at the target area (112). The CPU (114) controls operation of a radiation source (122), which may be a conventional linear accelerator, for directing radiation at the target area (112). The radiation source (122) includes a collimator (124) or similar apparatus for shaping a radiation beam for accurate application to the target area (112). A pair of RF receivers (126) and (128) are positioned such that they are spaced apart and opposite from the CPU antenna (120) with respective antennas (130) and (132) directed at the target area (112). Communication connections (133*a*), (133*b*), (133*c*), (133*d*) and (133*e*) interconnect the various elements of the system (110).

24 Claims, 8 Drawing Sheets

INCIDENT RADIATION

RADIATION DOSIMETRY SYSTEM

CROSS-REFERENCE TO RELATED APPLICATIONS

This application claims priority under 35 U.S.C. 119(e) from U.S. Provisional Patent Application Ser. No. 60/115, 192 filed on Jan. 6, 1999, having the same title as this application.

This application is related to co-pending U.S. patent application Ser. No. 09/321,862 entitled "X-RAY IMAGING APPARATUS USING SPHERICAL SEMICONDUCTOR DETECTORS," filed May 28, 1999; U.S. patent application Ser. No. 09/323,585 (U.S. Pat. No. 6,266,567) entitled "IMPLANTABLE EPICARDIAL ELECTRODE," filed Jun. 2, 1999; U.S. patent application Ser. No. 09/586, 073 entitled "METHOD AND APPARATUS FORTRACKINGPROJECTILES," filed Jun. 2, 2000; U.S. patent application Ser. No. 09/448,641 (abandoned) entitled "INTRALUMINAL MONITORING SYSTEM," filed Nov. 24, 1999; U.S. patent application Ser. No. 09/448,781 (abandoned) entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER," filed Nov. 24, 1999; U.S. patent application Ser. No. 09/448, 638 (U.S. Pat. No. 6,254,548) entitled "NTERNAL THERMOMETER," filed Nov. 24, 1999; U.S. patent application Ser. No. 09/448,644 (U.S. Pat. No. 6,264,611) entitled "MONITOR FOR INTERVENTIONAL PROCEDURES," filed Nov. 24, 1999; U.S. patent application Ser. No. 09/475, 820 entitled "MINIATURE IMPLANTED ORTHOPEDIC SENSORS," filed Dec. 30,1999; and U.S. patent application Ser. No. 09/706,276 entitled "THREE AXES ACCELEROMETER FOR MEDICAL AND HUMAN PERFORMANCE USES," filed Nov. 3, 2000, each of which or its earlier filed parent provisional is herein incorporated by reference.

TECHNICAL FIELD OF THE INVENTION

This invention is related to dosimeters, and more particularly, miniature dosimeters which are injectable into the human body.

BACKGROUND OF THE INVENTION

Radiation therapy is commonly used to destroy tumor cells in humans and animals. The idea is to deliver enough ionizing energy to destroy tumor cells but limit the amount of energy to avoid significant damage to surrounding normal cells and tissue. Radiation delivered to the tissue is calculated by measuring the energy output, the distance from the energy source to the target tissue, and the radiation absorption of the tissue that the radiation has to penetrate. Many assumptions, which are not always accurate, have to be made. Furthermore, the radiation delivered to one area of the target may be different from another area because of different tissue density and distance from the energy source. For example, radiation will penetrate through solid tissue differently from hollow tissue with air or hollow tissue with liquid. Although tumors on the surface of the skin are easy to dose accurately, tumors deep in a body cavity, such as the abdomen, chest, or brain cannot always be dosed precisely. Dosing can be particularly difficult in the pelvis, where several different types of structures exist with different densities, such as the bowel, ureter, blood vessels, and solid organs. Normal tissue is inevitably destroyed, often in a clinically significant manner because of the imprecise nature of the radiation-dosing procedures currently available. The consequences of imprecise radiation include ineffective treatment of tumors in cases of under-radiation, and destroying healthy tissue in cases of over-radiation. Serious complications such has vaginal-rectal fistulas can arise from radiating healthy tissue. In most other areas, tumor and the normal tissue are demarcated by a red marking pen on the skin when possible and the area for the radiation is calculated using physical properties of distance, which is again very imprecise.

Numerous radiation dosimeters have been proposed. For example, U.S. Pat. No. 4,381,450 by Cappelli, entitled "Pulsed Radiation Dosimetry Apparatus," issued Apr. 26, 1983, describes a pulsed radiation dosimetry apparatus utilizing a pin diode to detect pulsed radiation. The detected radiation signal is integrated and then displayed directly on a digital meter providing a direct readout of radiation dose in rads. U.S. Pat. No. 4,999,504 by Braunlich et al., entitled "Remote Radiation Dosimetry," issued Mar. 12, 1991, describes a remote radiation dosimetry apparatus using a beam generator, such as a laser beam, to provide a stimulating beam. The stimulating beam is used to stimulate a remote luminescent sensor mounted on a probe, which emits stored luminescent energy resulting from exposure of the sensor to ionizing radiation. The stimulating beam is communicated to the remote luminescent sensor via transmissive fiber which also serves to return the emission from the luminescent sensor. The stimulating beam is further split by a beam splitter to create a detector beam which is measured for power during a reading period during which the luminescent phosphor is read. The detected power is then used to control the beam generator and thus produce the desired beam power. U.S. Pat. No. 5,115,134 by Slowey, entitled "Precise Low Energy Radiation Dosimetry," issued May 19, 1992, describes a precise low energy radiation dosimetry system using an ionization chamber with a beryllium window. A conductive carbon coating, including lithium and fluorine, provides secondary electron emissions to flatten response of the beryllium window in the desired radiation energy range without the use of external mathematical correction factors.

U.S. Pat. No. 5,637,876 by Donahue et al., entitled "Radiation Dosimetry Method and Apparatus," issued Jun. 10, 1997, describes a radiation dosimetry apparatus comprising a substrate that is radiation sensitive and has optical density which varies in accord with the degree of radiation exposure. The substrate is also provided with an optically readable code, which identifies encoded mathematical parameters to enable an automated calculation dosage from a detected post-exposure optical density of the radiation sensitive material. Each dosimeter is provided with a unique identification code encoded in the bar coding on the dosimeter substrate.

This enables memory storage of pre-exposure optical density as a baseline reference to be used in order to calculate the radiation dose when compared to the postexposure density. U.S. Pat. No. 5,767,520 by Donahue et al., entitled "Radiation Dosimetry Method and Apparatus," issued Jun. 16, 1998, describes a plurality of pre-exposure optical densities and a plurality of post-exposure optical densities of the layer of radiation sensitive material in a plurality of wavelength bands to allow optical measurement of the radiation dose at multiple time periods. U.S. Pat. No. 5,811,822 by Huston et al., entitled "Optically Transparent, Optically Stimulable Glass Composites For Radiation Dosimetry," issued Sep. 22, 1998, describes an optically transparent and optically stimulable glass composite for radiation dosimetry. In this invention, a glass matrix is doped with various radiation sensitive elements. An article entitled "General Specifications for Silicon Semiconductors for Use in Radiation Dosimetry," by Swedish researchers Rikner and Grusell, published in PHYsics MEDICINE BIOLOGY, Vol. 31, No. 9, 1109–1117, ©1987 IOP Publishing Ltd., describes the characteristics of diodes used as radiation detectors.

All of the above references describe a radiation dosimetry system capable of detecting and quantifying the radiation dose. However, all but one of the above references describe a dosimeter that must be directly and physically accessible. This requires the dosimeter to be on the surface of the patient and thus, the previous patents have limited clinical application, particularly in tumors that are seated deep in the chest or abdomen. Although the abovementioned U.S. Pat. No. 4,999,504 allows remote sensing by using laser beams, lasers can only penetrate tissue to a limited depth. Furthermore, none of the above inventions allows precise determination of the location of the sensor in the depths of the body.

All of the previous inventions measure radiation in a one-dimensional surface and do not consider radiation in all directions, including scatter. The dosimeters are large and cannot be placed in many multiple sites.

SUMMARY OF THE INVENTION

The present invention disclosed and claimed herein, in one aspect thereof, comprises a system for detecting a dosage of radiation received by a tumor during radiation treatment. A radiation source is directed at the tumor. A central processing unit connects to the radiation source for monitoring and controlling the radiation treatment. One or more dosimetry transponders are injected into the tumor, each the dosimetry transponder having, a communication circuit for communicating power and control signals between the transponder and the central processing unit, and one or more detectors for detecting radiation and converting the detected radiation to a data signal.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

The disclosed architecture provides a system for directly measuring radiation during tumor treatment using a miniature implantable or injectable transponder that is capable of detecting and quantifying the radiation dosage, and transmitting such data by radio frequency signals to an external central processing unit. The transponder is preferably fabricated using the techniques described in commonly-assigned U.S. Pat. No. 5,995,776 entitled "Spherical Shaped Semiconductor Integrated Circuit," and issued Sep. 21, 1999, which is hereby incorporated by reference. The transponder can also be encoded with a unique identification code to allow identification of each individual transponder. A position sensing system precisely locates each spherical transponder using radio frequency transmission signals, which allows precise measurement of radiation dosing in specific areas of the tumor as well as surrounding normal tissue. The spherical sensors are functional in all directions, sense radiation that is scattered, and more accurately reflect the total radiation absorbed by the tissue. Such a system allows the physician to determine the precise radiation dose delivered to a target tumor located anywhere in the body, such as the brain cavity, cranium, chest, or abdomen, for more efficient tumor destruction. The physician can determine the optimal radiation dose to maximize tumor destruction and minimize collateral damage to surrounding healthy tissue.

Furthermore, the small size and substantially spherical shape of the transponder allows it to be injected or surgically implanted more precisely into various sites of the tumor or surrounding tissue, or to be injected using needles or through a catheter into the feeding blood vessel of the tumor or other body cavities. The dosimetry transponders are near microscopic and easy in implant in multiple sites without much pain and discomfort to the patient. The transponder is placed or implanted at the site of the tumor to measure the radiation dosage received into the tumor, and placed or implanted in the normal surrounding tissue (skin or deep structures) of the tumor to measure the exposure to collateral healthy tissue. The dosage and the placement of the radiation beam can then be appropriately adjusted. Particularly, deep-seated tumors and the surrounding tissue can be monitored more precisely for radiation dosing during the procedure.

Figure 1:
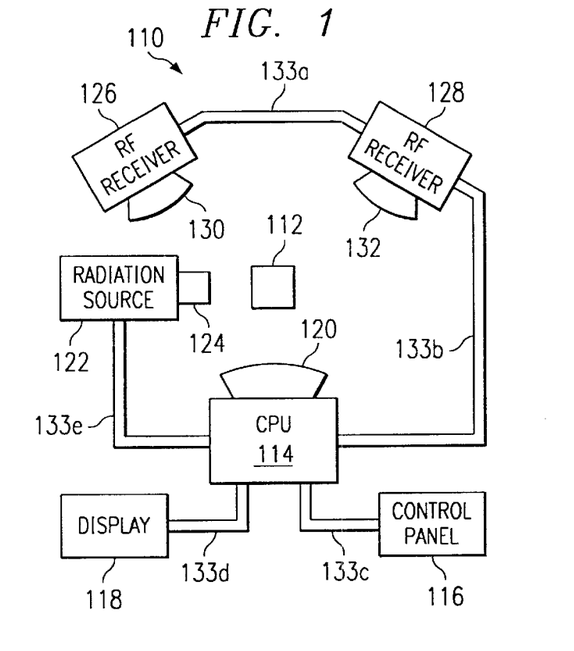
FIG. 1 illustrates a diagram of a radiation dosimetry system, in accordance with a disclosed embodiment.

Referring now to FIG. 1, there is illustrated a diagram of a radiation dosimetry system 110 in accordance with a disclosed embodiment. A patient with a tumor that is the target of the radiation treatment lies still in a treatment area with the tumor positioned beneath a target (or frame) 112 used for alignment purposes. The system 110 is controlled and monitored by a central processing unit (CPU) 114, which receives instructions from a control panel 116 and displays control parameters, data and graphics on a display 118. The CPU 114 is equipped with a radio frequency (RF) system operating through a broad-band antenna 120 and directed at the target area 112. The CPU 114 controls operation of a radiation source 122, which may be a conventional linear accelerator, for directing radiation at the target area 112. The radiation source 122 includes means for shaping a beam of radiation, such as a collimator 124, in accordance with known techniques. A pair of RF receivers 126 and 128 are positioned such that they are spaced apart and opposite from the CPU antenna 120 with respective antennas 130 and 132 directed at the target area 112. Data cables 133a, 133b, 133c, 133d and 133e interconnect the various elements of the system 110.

During treatment, the CPU 114 polls each of the transponders 236 and 238 by individually addressing them according to their respective stored unique ID codes. Notably, the transponders 236 and 238 may also be queried sequentially according to their respective unique ID codes. Each transponder 236 and 238 in turn sends out a signal that is received by the CPU 114 and the RF receivers 126 and 128 that allows its location to be identified and superimposed on a fluoroscopic map of the tumor 234 on the display 118. The radiation source 122 then directs a beam of radiation at the tumor 234 positioned in the target area 112. A short initial registration radiation burst is used to determine if the radiation beam is in the target area 112 and if the dosage received by the tumor 234 is appropriate. The external transponders 238 that are located outside, but close to the tumor 234 provide an indication of the peripheral radiation dosage that is being received into the nearby normal healthy tissue. This peripheral dosage level should be maintained below a predetermined threshold level so as to avoid injury to healthy tissue. Each of the one or more transponders 236 and 238 report back to the CPU 114 in response to a query by the CPU 114, the dosage level it is experiencing during the initial registration burst. This information can be displayed by the CPU 114 on the display 118 to confirm that the radiation beam is properly aligned and oriented, and that the dosage level is within a preset range determined to be appropriate for the particular procedure. Thus, a precise determination of the radiation dosage level and its impact on the tumor 234 and surrounding tissue can be determined.

Figures 2, 3:
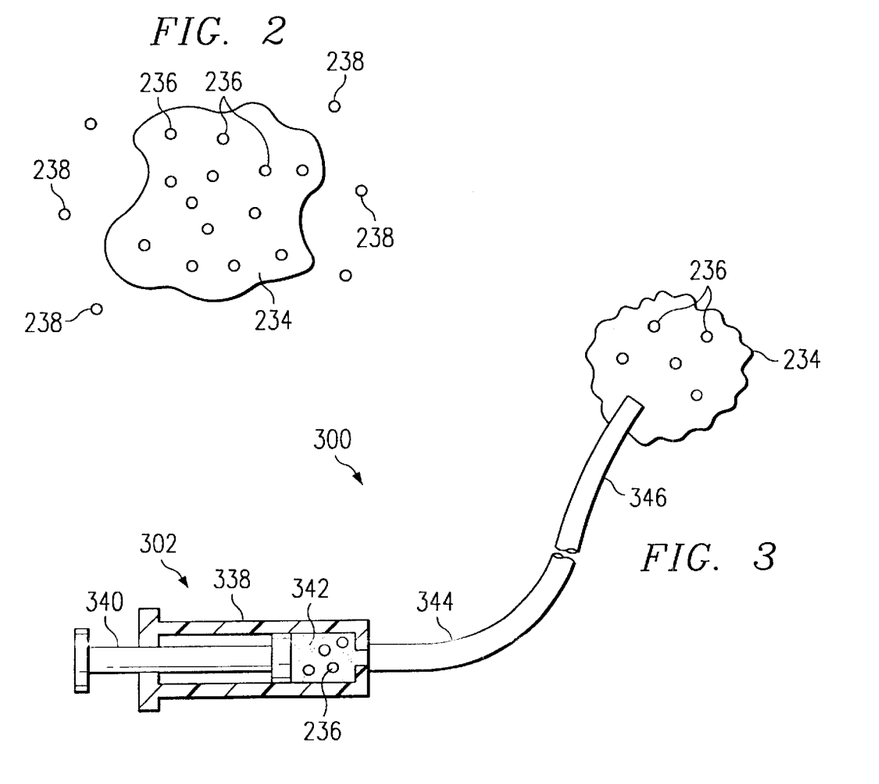
FIG. 2 illustrates a diagram of a tumor with a slurry of internal dosimetry transponders implanted therein, and dosimeters external to the tumor.
FIG. 3 illustrates a catheter delivery system for injecting the dosimetry transponders into the tumor.

Referring to FIG. 2, there is illustrated a diagram of a tumor 234 with a slurry of internal dosimetry transponders 236 implanted therein. Additional external dosimetry transponders 238 are injected into normal healthy tissue which is outside of the tissue mass that defines the tumor 234. The number of internal transponders 236 injected into the tumor 234 is determined by the size of the tumor, and the precision required to obtain the desired result. For example, the more internal transponders 236 used, the more precise the radiation treatment will be, since the greater number of transponders 236 will better define the boundaries of the tumor 234. However, there is a limit to the number which can be used, as determined by the size and structure of the tumor. The precision is determined from the feedback received by the available number of injected transponders 236 which are continuously queried for radiation levels during the procedure. Referring to FIG. 3, there is illustrated a catheter delivery system 300 for injecting the dosimetry transponders 236 into the tumor 234. The catheter delivery system 300 includes a specialized syringe 302 consisting of a housing 338 and a plunger 340. The housing 338 (shown in cross-section) includes a cylindrical chamber within which a slurry 342 of internal transponders 236 resides. Forcing the plunger 340 into the housing 338 causes the slurry 342 to be delivered to the tumor 234 through a catheter 344. The catheter 344 is shown broken away for convenience of illustration, with a distal end 346 extending into the tumor 234. The catheter 344 can be fed through the patient's arteries to the tumor 234, using known techniques. Further discussion of such catheter insertion techniques is included in the commonly-assigned and pending U.S. patent application Ser. No. 09/475,819 (Atty. Dkt. No. BASI-24,791) entitled "Injectable Thermal Balls for Tumor Ablation," filed Dec. 30, 1999.

Figure 4A:
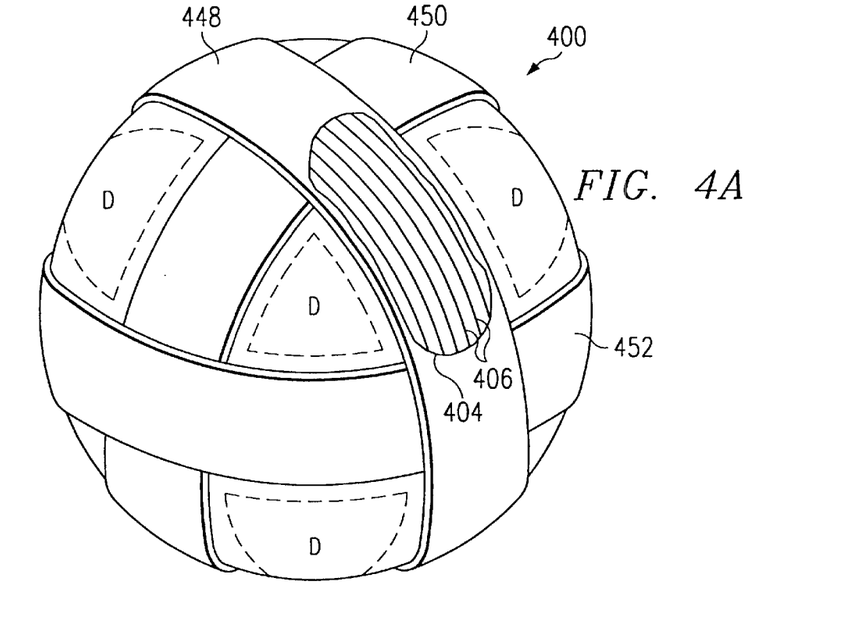
FIG. 4A illustrates a geometrical view of a dosimetry transponder.

Referring now to FIG. 4A, there is illustrated a geometrical view of a dosimetry transponder 400. The dosimetry transponder 400 (similar to both the internal transponder 236 and the external transponder 238 mentioned hereinabove) includes three bands 448, 450 and 452 of coils that extend around a substantially spherical-shaped semiconductor substrate (the substrate not indicated), which substrate may be fabricated using techniques described in the abovementioned U.S. Pat. No. 5,995,776 entitled "Spherical Shaped Semiconductor Integrated Circuit." For example, band 448 illustrates a more detailed cutaway 404 of six coils 406. Notably, the band 448 may include more or fewer coils 406, according to the particular application. Each band 448, 450, and 452 is substantially orthogonal to one another to facilitate coupling of power and signals thereto, and signals and data therefrom, in any orientation which the transponders 236 and 238 may rest. Further discussion of this feature is described in the above-referenced U.S. Patent application entitled "Position Sensing System." Radiation-sensitive diodes D, defined by the dash lines, are arranged in the spaces not covered by the bands of coils 448, 450 and 452. Such radiation-sensitive diodes are described in W Zhao and J. A. Rowlands, "A Large Area Solid-State Detector for Radiology Using Amorphous Selenium," SPEE Vol. 1651, MEDICAL IMAGING VI INSTRUMENTATION (1992) TO 134–143, which is incorporated herein by reference.

Figure 4B:
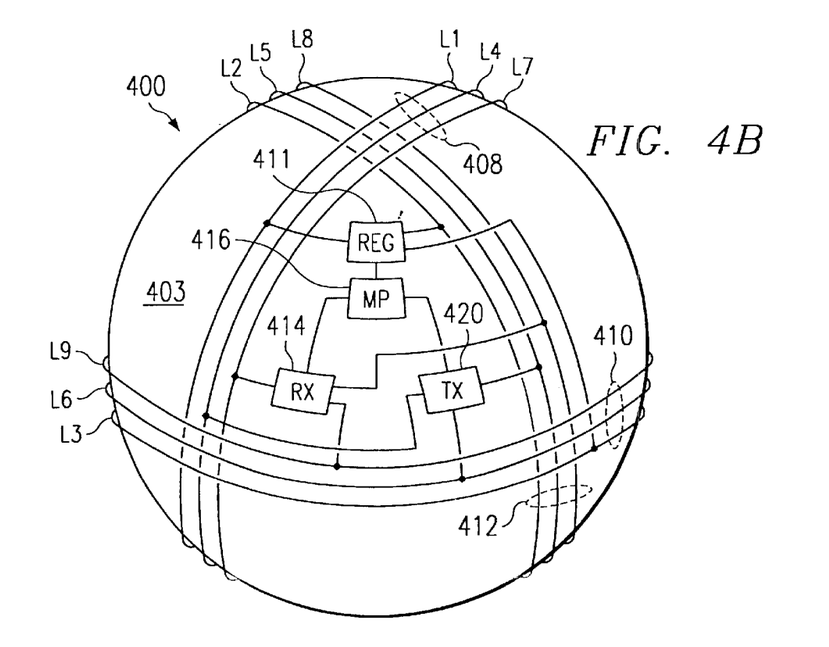
FIG. 4B illustrates a more detailed spherical geometry of a transponder showing onboard control electronics, according to a disclosed embodiment.

Referring now to FIG. 4B, there is illustrated more detailed spherical geometry of the transponder of FIG. 4A showing onboard control electronics, according to a disclosed embodiment. The transponder 400 is fabricated on a substantially spherical substrate 403, and includes nine coils $L_1$–$L_9$ in three sets 408, 410, and 412 of three coils, each set 408, 410, and 412 preferably substantially orthogonal to each other so that power and signal communication requirements can be optimized according to the any resulting orientation of each transponder ball 400. Each coil set 408, 410, and 412 comprises three coils; one transmit coil, one receive coil, and a power coupling coil. Therefore, in this embodiment, there are three power coils $L_1$, $L_2$, and $L_3$; three transmit coils $L_4$, $L_5$, and $L_6$; and three receive coils $L_7$, $L_8$, and $L_9$. The coils sets 408, 410, and 412 are grouped in this fashion to ensure that at least one coil set 408, 410, or 412 is orientated to provide potentially optimum power coupling and signal communication therewith. Onboard circuitry comprises a processor circuit (MP) 416 for controlling all aspects of the transponder ball 400. The processor circuit 416 can be a digital signal processor or other conventional processors.

Power for the transponder 400 is provided via a regulator circuit 411 which regulates power coupled into any of the power coils $L_1$, $L_2$, and $L_3$. Communications are provided by a transmit circuit 420 and a receive circuit 414. The transmit circuit 420 connects to the three transmit coils $L_4$, $L_5$, and $L_6$ in order to provide transmit communications which are capable of outputting signals in any orientation of the transponder 400, and only one of which is included in one of the three sets of coils 408, 410, and 412. Similarly, the receive circuit 414 connects to each of the receive coils $L_7$, $L_4$, and $L_9$, in order to provide receive communications which are capable of receiving signals in any orientation of the transponder 400, and only one of which is included in each one of the three sets of coils 408, 410, and 412. The coils $L_1$–$L_9$ can have any number of windings (not shown) in order to achieve the desired results. Notably, the coils sets 408, 410, and 412 could also be configured to each have only one particular coil function associated therewith. For example, coil 408 could be dedicated exclusively to power coupling, coil 410 could be dedicated exclusively to signal receive functions, and coil 412 could be dedicated exclusively to signal transmission functions.

The coils $L_1$–$L_9$ are connected by subsurface conductors (not shown) to the other circuit elements on the transponder 400. The processor 416 provides an output to the transmitter 420 that preferably radiates an RF signal to the external antenna 120 for processing by the CPU 114. The power regulator 411 provides a relatively constant DC voltage of about 3.0 volts to the circuits on the transponder 400. A disclosed power source for the transponder 300 is provided by the CPU 112 in conjunction with the antenna 120 which couples power to the power coils $L_1$, $L_2$, and $L_3$ in the form of a varying magnetic field. Alternatively, the transponder 400 can be powered by a miniature battery connected to the transponder 400 (which is discussed in greater detail hereinbelow). The miniature battery can also be in the shape of a ball (battery ball) configured to accommodate a common connection scheme for use between adjacent balls. Preferably, battery balls can be fashioned as electrical double-layer condensers from such materials as manganese dioxide, lithium or lithium ion, samarium-cobalt, carbon, etc. Since such a battery ball is a greater capacity energy source than an RF energy receiving coil, longer communication distances can be achieved by this means. Both the external magnetic field generator (CPU system 114) and receiver antenna 120 can be included in the same computer-controlled apparatus or CPU station within proximity of the transponder 400, at least, but not limited to periods when its operation is required.

Figure 4C:
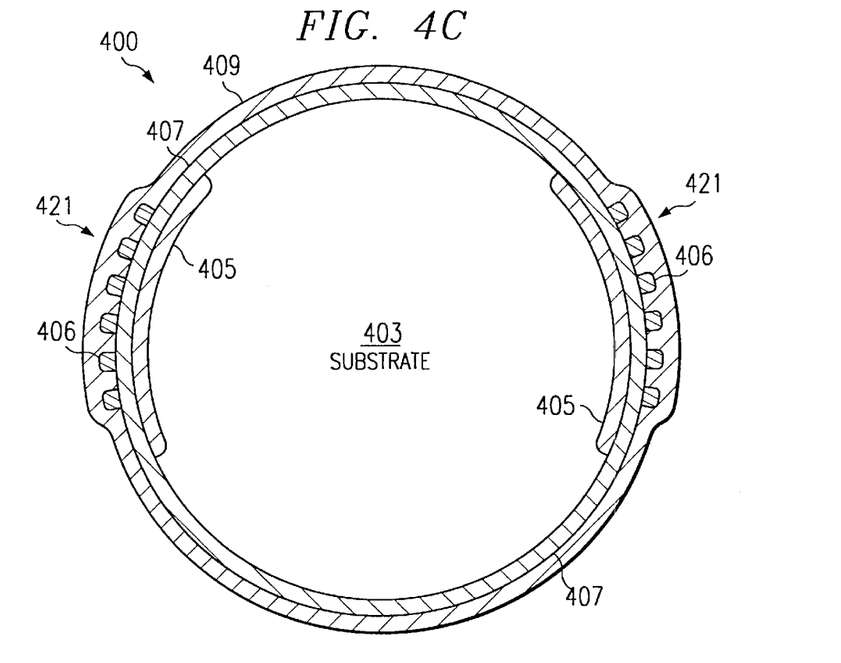
FIG. 4C illustrates a coss section of a transponder ball, preferably comprising a spherical-shaped semiconductor device on which an integrated circuit has been formed.

Referring now to FIG. 4C, there is illustrated a coss section of a transponder ball, preferably comprising a spherical-shaped semiconductor device on which an integrated circuit has been formed. Such a spherical-shaped integrated circuit semiconductor device (sometimes referred to herein as a "ball") is described in commonly assigned, U.S. Pat. No. 5,955,776, issued Sep. 21, 1999, and entitled "Spherical Shaped Semiconductor Integrated Circuit," the disclosure of which is referenced hereinabove. Transponder 400 is built on the substantially spherical semiconductor substrate 403, which may be doped P-type or N-type in accordance with the particular requirements of the fabrication process. Semiconductor circuitry indicated generally at 405 resides on the substrate 403. Circuitry 405 includes the elements illustrated in FIG. 4B, including the power regulator 411, the transmit and receive circuits 414 and 420, the processor 416, as well as other circuitry. The substrate 403 and circuitry 405 are covered with an insulating layer 407 which is preferably formed of silicon dioxide or phosphosilicate glass (PSG). A power coil 421 (one of $L_1$, $L_2$, and $L_3$), and described with respect to FIG. 4B, is formed of helically wrapped windings over an insulating shell 407. The power coil 421 may be fabricated from a deposited layer of aluminum that is patterned and etched using conventional semiconductor fabrication techniques. The actual number of individual windings 406 of power coil 421 may be more or less than the six shown in FIG. 4C.

The transponder 400 is coated with or encapsulated in a coating layer 409 of a biological inert material such as phosphosilicate glass. The coating 409 is inert and can withstand potential chemical degradation into which it contacts, for example, the acidity of the stomach, to a very low pH level, and it is not subject to the enzymatic actions of the digestive tract. Transponder 400 is substantially spherical and preferably about one millimeter in diameter. The very small size of transponder 400 enables it to be injectable, implantable in human tissues and cavities, and embeddable in surgical or medical tools, and apparatus.

Figure 5:
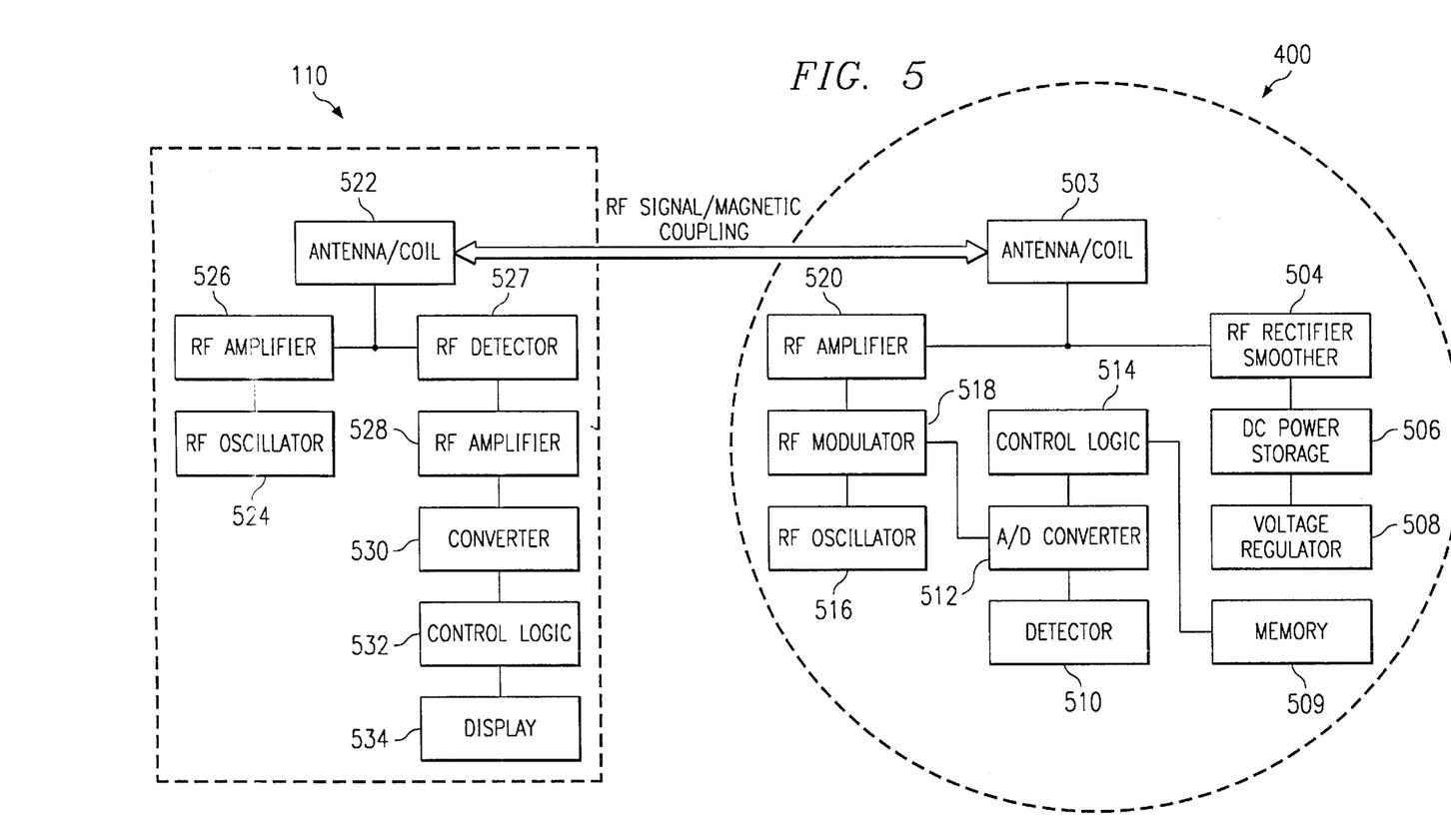
FIG. 5 illustrates a more detailed block diagram of an alternative embodiment of a control system and transponder having more complex integrated circuitry.

Referring now to FIG. 5, there is illustrated a more detailed block diagram of an alternative embodiment of a control system and transponder having more complex integrated circuitry. The transponder 400 (similar to transponders 236 and 238) includes circuitry for receiving power by magnetic coupling from the radiating antenna 120 and transmitting data by RF transmission to the remote receivers 126 and 128 in the external dosimetry system 110. The basic circuit functions performed by the semiconductor transponder ball 400 are illustrated, and designated generally by reference numeral 400, and which communicate with the receiver/transmitter elements of the dosimetry system 110.

The transponder 400 includes an antenna/coil 503, which serves the dual purpose of receiving power from the station 502 and transmitting data on an RF carrier signal to the system 110. The power may be received by the antenna/coil 503 by direct magnetic coupling, if the system 110 is sufficiently close to the transponder 400. Alternatively, an electromagnetic wave can be used to transmit power from the system 10 to the transponder 400, whereby the magnetic field component of the electromagnetic wave induces a current in the coil 503, in accordance with known techniques. The power signal received by the antenna/coil 503 is rectified and smoothed by an RF rectifier smoother circuit 504. The output of the rectifier circuit 504 is connected to a DC power storage device 506, such as a capacitor. Such capacitor might also be of assistance in performing the waveform smoothing function. A voltage regulator 508 is used to make the DC voltage stable regardless of the distance between the system 110 and the transponder 400. For example, a Zener diode or other suitable clamping circuit can perform this function. The resulting DC voltage is supplied to all circuits of the transponder 400. In this particular embodiment, the transponder 400 also includes at least one detector 510 for sensing radiation dose levels. It will be appreciated that more than one detector 510 can be constructed on the transponder 400.

If a sensor were also included on the transponder 400, a condition or parameter of the environment in which the transponder 400 is located can be sensed. For example, pressure can be sensed through a change in capacitance or resistance. Such semiconductor pressure transducers are known in the art and can be adapted to fabrication on the spherical semiconductor substrate 403. A variable-resistance strain gauge is disclosed in commonly-assigned U.S. patent application Ser. No. 09/448,641 (Atty. Dkt. No. BASI-24, 783), entitled "Intraluminal Monitoring System," and filed on Nov. 24, 1999, which is hereby incorporated by reference. Thermal balls having heating capabilities and corresponding temperature sensors are disclosed a co-pending U.S. patent application Ser. No. 09/475,819 (Atty. Dkt. No. BASI-24,791) entitled "Injectable Thermal Balls For Tumor Ablation," filed Dec. 30, 1999. It will be appreciated that multiple sensors and detectors can be placed on a single transponder 400 where more than one condition or parameter of the environment of the transponder 400 is sensed. For example, temperature, as well as pressure sensing, and electrical stimulation can be provided by suitable means on a single transponder 400.

In another application, the transponder 400 is used to stimulate excitable tissue. The semiconductor ball can function as a TENS (Transcutaneous Electrical Nerve Stimulator) unit. This is very important in treating chronic pain syndromes. The unit can also be used to stimulate both nerve and muscles in paralyzed or injured limbs to help prevent the development of atrophy or as a means to reduce the inflammatory response. Multiple balls which function as both receivers of electrical signal and also as transmitters of signal could function as a bridge between an amputated limb and a moveable prosthetic "hand." In the case of an actuator, a stimulus circuit applies an electrical stimulus to the desired medium under control of the system 110 to the tissue or medium in which it comes in contact, during the position sensing function, and while the temperature of the surrounding tissues is being measured. For example, a certain medical procedure may require that stimulus be provided to an anatomical structure to increase or decrease separation from another structure. Using the disclosed position sensing system in cooperation with an onboard stimulus generator can facilitate this type of medical procedure. A separate actuator signal may need to be transmitted to the transponder 400, in addition to the power signal for powering the transponder 400. The transmitted actuator signal is then processed by an onboard control logic circuit 514 to control the stimulus circuit to perform the desired function. Such a stimulator circuit is disclosed in commonly-assigned U.S. patent application Ser. No. 09/475,820 (Atty. Dkt. No. BASI-24,794) entitled "Miniature Implanted Orthopedic Sensors," filed Dec. 30, 1999.

A memory 509 connects to the control logic 514, and provides onboard storage of, for example, a unique transponder ID, patient information, procedure information, or any information deemed necessary for storage on the transponder 400. A converter 512, which may be an A/D converter, is used to convert the condition sensed by the detector 510 to a signal that can be transmitted out to the system 110. The converter 512 can be part of the detector 510 (such as a variable capacitor for generating a signal depending upon the variations in capacitance). The control logic 514, which can be part of an onboard processor that controls not only the converter 512, but also other circuitry on the transponder 400, is provided in accordance with known techniques. An RF oscillator 516 generates a radio-frequency carrier signal at a predetermined frequency in the RF band. An RF modulator 518 modulates the output of the converter 512 onto the carrier frequency signal. The resulting modulated signal is amplified by RF amplifier 520, and then transmitted external to the body through the antenna/coil 503. The illustrated antenna/coil block 503 represents one or more of the coil sets 408, 410, and 412, the power, transmit and receive coils $L_1$–$L_9$.

The system 110 includes an antenna/coil 522 that serves the dual purpose of generating the electromagnetic wave for transmitting power to the transponder 400, and receiving the RF data signal transmitted by the transponder 400. It is preferred that the frequency of the electromagnetic wave that is output by the antenna/coil 522 is different from the carrier frequency generated by an RF oscillator 524. An RF amplifier 526 is used to couple the electromagnetic wave for power transmission to the antenna/coil 522. The frequency of the electromagnetic wave that is output by the system 110 is determined by the RF oscillator 524. The data signal received by the antenna/coil 522 is detected by an RF detector 527 and then amplified by an RF amplifier 528. Preferably, the signal from the RF amplifier 528 is converted by a converter 530 to a digital signal, which in turn is input to control logic 532. The control logic 532 may be a special-purpose CPU, or an interface to a general-purpose CPU or computer. The control logic 532 extracts the data from the signal received by the system 110 from the transponder 400, and displays that information on a suitable display 534, such as a CRT screen. The technique for transmitting data from the transponder 400 to the system 110 using the carrier frequency generated by the RF oscillator 516, can be in any form, using any suitable protocol. The modulation can be, for example, AM, FM, PM or any other suitable modulation technique.

Although a single transponder 400 can include the foregoing functions, more complex monitoring functions with multiple transducers and detectors can be implemented using multiple ball systems attached to catheters, needles and other insertable devices. These systems can be affixed to body surfaces, or can be attached to catheters, needles, and other insertable devices. In the case of insertable devices, these systems can be arranged so as to remain fixed at a specified site, or can be permitted to be transported through body conduits by various means, including convection, peristalsis, diffusion, etc.

Figure 6:
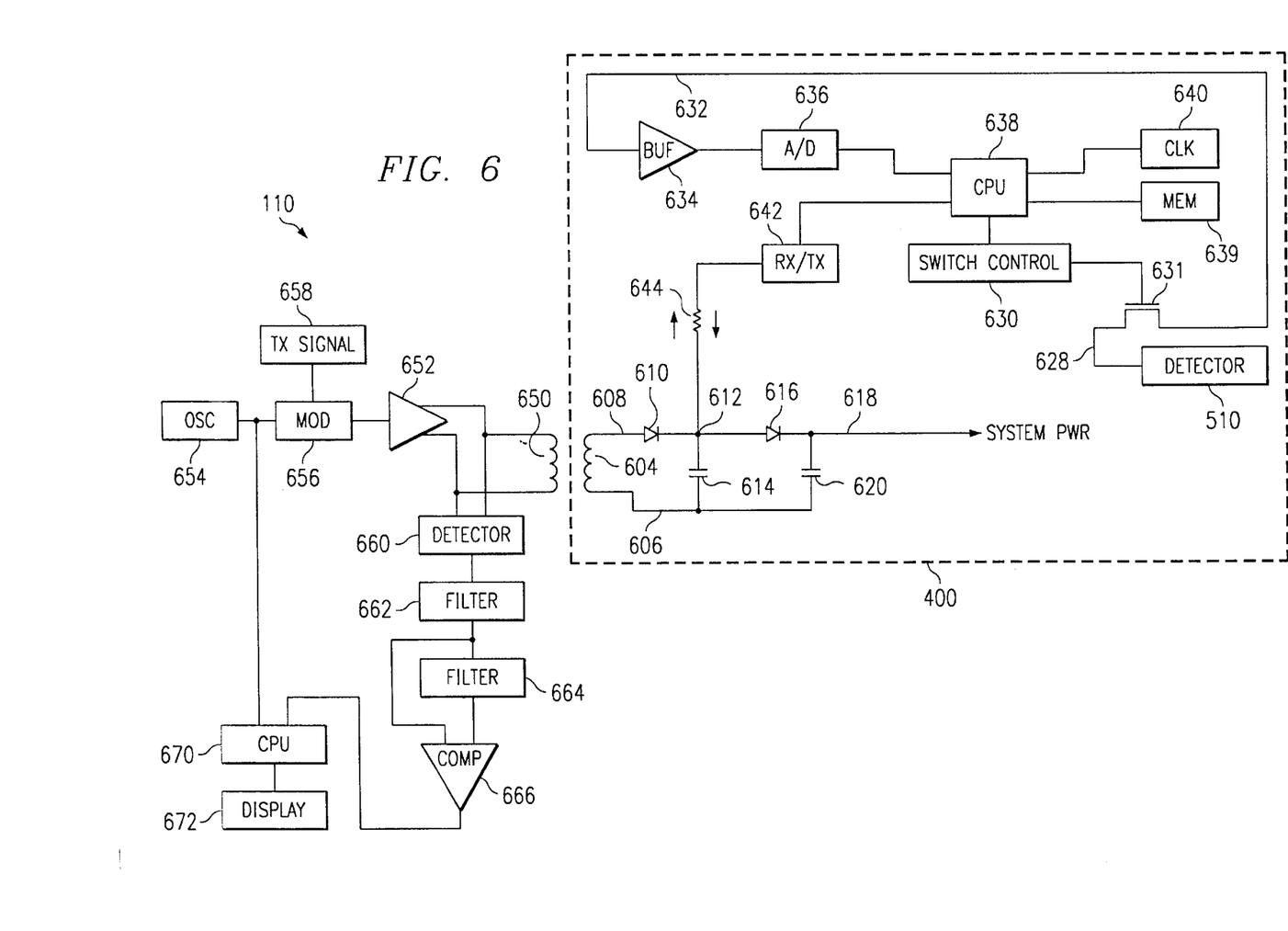
FIG. 6 illustrates a schematic block diagram of the transponder and the control system of FIG. 5.

Referring now to FIG. 6, there is illustrated a schematic block diagram of the transponder 400 and the control system 110 of FIG. 9. The ball transponder 400 is operable to provide the transmit/receive functions associated with a disclosed transponder embodiment, and for interfacing with the desired quantitative condition. The illustrated embodiment of FIG. 6 is that associated with a "passive" system, which term refers to a system having no battery associated therewith. In order to operate the system, there is provided an inductive coupling element 604 in the form of an inductor, which is operable to pick up an alternating wave or impulse via inductive coupling, and extract the energy therein for storage in the inductive element 604. This will create a voltage across the inductive element 604 between a node 606 and a node 608. A diode 610 is connected between the node 608 and the node 612, with the anode of diode 610 connected to node 608 and the cathode of diode 610 connected to a node 612. Typically, the diode 610 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 610 is operable to rectify the voltage across the inductive element 604 onto the node 612, which has a capacitor 614 disposed between node 612 and node 606. Node 612 is also connected through a diode 616 having the anode thereof connected to node 612 and the cathode thereof connected to a node 618 to charge up a capacitor 620 disposed between node 618 and 606. The capacitor 620 is the power supply capacitor for providing power to the transponder 400. The capacitor 614, as will be described hereinbelow, is operable to be discharged during operation of the system and, therefore, a separate capacitor, the capacitor 620, is required for storing power to power the system of the transponder 400.

There is also provided a switching transistor 631 which has one side of the gate/source path thereof connected to a node 628, which is the output of the detector 510 and the other side thereof connected to a node 632. The gate of transistor 631 is connected to the output of a switch control 630. Node 632 is connected to the input of a buffer 634 to generate an analog signal output thereof which is then converted with an analog-to-digital converter 636 to a digital value for input to a CPU 638 (comprised in control logic 514, and similar to processor 416). The CPU 638 is operable to receive and process this digital input voltage. A clock circuit 640 provides timing to the system. A memory 639 is provided in communication with the CPU 638 to allow the CPU 638 to store data therein for later transmittal back to the system 110 or for even storing received instructions. This memory 639 can be volatile or it can be non-volatile, such as a ROM. For the volatile configuration, of course, this will lose all information when the power is removed. The memory 639 is also operable to store preprogrammed information such as a unique ID, patient information, physician information, or any information desired according to the particular procedure and function of the transponder 400. The CPU 638 is operable to provide control signals to the switch control 630 for turning on the transistor 631 at the appropriate time. In addition to the transistor 631 being toggled to read the detector 510, transistor 631 could be a pass-through circuit such that the CPU 638 can continually monitor the voltage at the output of the detector 510. System power to all power-consuming elements of the ball transponder 400 is provided at the SYSTEM PWR output node.

In order to communicate with the CPU 638 for transferring data thereto and for allowing the CPU 638 to transfer data therefrom, a receive/transmit circuit 642 (similar to the receive and transmits circuit 314 and 320, respectively) is provided for interfacing to node 612 through a resistive element 644. This allows RF energy to be transmitted to node 612. It is important to note that the semiconductor junction across diode 610 is a capacitive junction. Therefore, this will allow coupling from node 612 to node 608. Although not illustrated, this could actually be a tuned circuit, by selecting the value of the capacitance inherent in the design of the diode 610. In any event, this allows an RF connection to be provided across diode 610 while allowing sufficient energy to be input across conductive element 604 to provide a voltage thereacross for rectification by the diode 610 and capacitor 614. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al., U.S. Pat. No. 3,944,982, entitled "Remote Control System For Electric Apparatus," issued Mar. 16, 1976, which are incorporated herein by reference. With these types of systems, power can continually be provided to the node 612 and subsequently to capacitor 620 to allow power to be constantly applied to the ball transponder 400.

The external system 110, which is disposed outside of the body and proximate to the ball transponder 400, includes an inductive element 650 which is operable to be disposed in an area proximate to the skin, yet exterior to the body, in the proximity of the transponder 400. The inductive element 650 is driven by a driving circuit 652 which provides a differential output that is driven by an oscillator 654. This will be at a predetermined frequency and power level necessary to couple energy from inductive element 650 to inductive element 604. Since this is an external system, the power of the oscillator can be set to a level to account for any losses through the body tissues. To allow information to be transmitted, a modulation circuit 656 is provided which is modulated by a transmitter signal in a block 658 that allows information to be modulated onto the oscillator signal of the oscillator 654, which oscillator signal is essentially a "carrier" signal. However, it should be understood that the information that is transmitted to the transponder 400 could merely be date information, whereas the CPU 638 could operate independent of any transmitted information to provide the correct timing for the output pulses and the correct waveshape therefor.

Alternatively, entire control of the system could be provided by the transmit signal 658 and the information carried thereon, since power must be delivered to the illustrated embodiment due to the lack of any independent power in the transponder 400. Note also that the distance of the remote system 110 to the transponder 400 may need to be varied such that the power signal coupled to the transponder 400 is of sufficient energy to receive an RF signal back from the transponder 400. The strength of the signals exchanged between the transponder 400 and the control system 110 varies according to the number of tissues and body parts between the transponder 400 and the control system 110. For example, where a transponder 400 is introduced in a vein close to the surface of the skin, the signal strength is less likely to be affected since the control system 110 can be placed very closely to the transponder 400. On the other hand, where the transponder 400 is introduced into an artery near the heart, the signal strength of the control system 110 may need to be increased to power the transponder 400. Alternatively, where the power output of the control system 110 is limited, the antenna mechanism 120 may need be inserted into the body to come into closer proximity of the transponder 400.

When the information is to be transmitted from the transponder 400, it is superimposed upon the oscillator signal driving the inductive element 604 and coupled across to the control system antenna inductor element 650. This is extracted therefrom via a detector 660 which has the output thereof input to a first low pass filter 662, and then to a second low pass filter 664. The output of low pass filters 662 and 664 are compared using a comparator 666 to provide the data. The filter 662 provides an average voltage output, whereas the filter 664 provides the actual digital voltage output. The output of the comparator 666 is then input to a CPU 670 which also is powered by the oscillator 654 to process the data received therefrom. This can then be input to a display 672.

Figure 7:
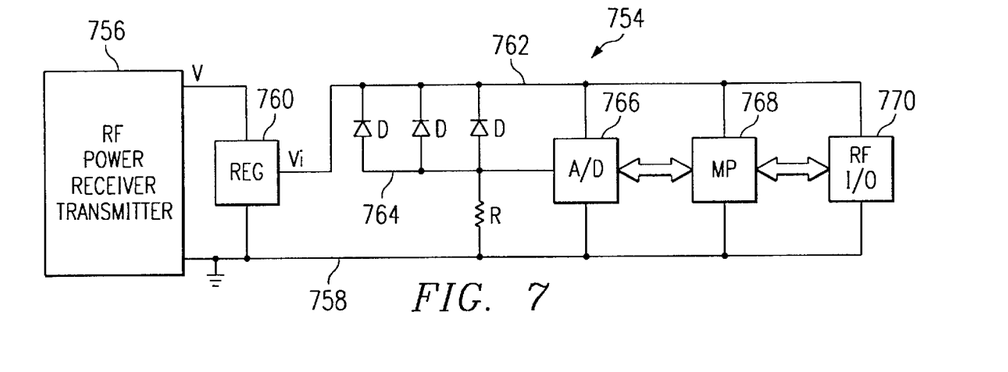
FIG. 7 illustrates a circuit diagram of the transponder.

Referring now to FIG. 7, there is illustrated a circuit diagram for the transponder 400. A transponder circuit 754 includes an RF power receiver 756, which includes coils (e.g., coils 406, 408, and 410) for inductively receiving RF energy that is converted to a voltage V above an internal ground potential 758. The voltage V is converted to an internal operating voltage $V_i$ by a voltage regulator (REG) 760 (similar to the regulator circuit 411 and 508). The internal voltage $V_i$ is supplied to other circuitry of the transponder 400 along a voltage supply rail 762. The voltage $V_i$ reverse-biases diodes D, which are connected in parallel, and only three of which are shown, although additional diodes D may be included to obtain the desired results. One end of a resistor R is connected to a node 764 common to the anodes of the diodes D, and at the other end to a ground rail 758. The node 764 provides a reference voltage to an analog-to-digital (A/D) converter 766 (similar to A/D 512). The output of the A/D converter 766 is provided to a microprocessor (MP) 768 (similar to control logic 514 and CPU 638). The microprocessor 768 includes a memory (not shown, but similar to memory 639) that stores a unique serial number (or "ID" code) for identifying the particular transponder 400. The microprocessor 768 controls data communications from and to the transponder 400 by means of an RF input/output (I/O) circuit 770 (similar to the combined functions of circuits 516, 518, and 520, and transmit/receive circuit 642).

In operation, the patient's tumor 234 is injected with the internal transponders 236. External transponders 238 are either injected into the normal tissue in the vicinity of the tumor 234, or are taped to the skin of the patient nearest the site of the tumor 234. Injection of the external transponders 238 can be achieved using a syringe. The external transponders 238 can be configured similar to the structure of the internal transponders 236, to include transponder circuitry 754. After the patient has been treated in this manner and has been positioned properly in the target area 112, the radiologist at the control panel 116 then assumes control of the procedure.

Figure 8A:
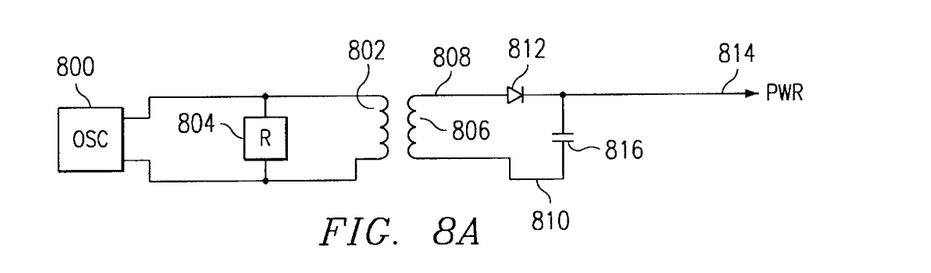
FIGS. 8A–C illustrate alternate embodiments for the transmit/receive operation.
Figure 8B:
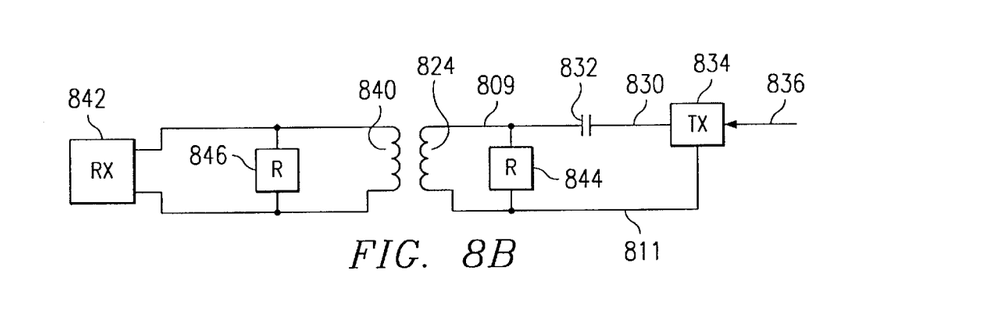
Figure 8C:
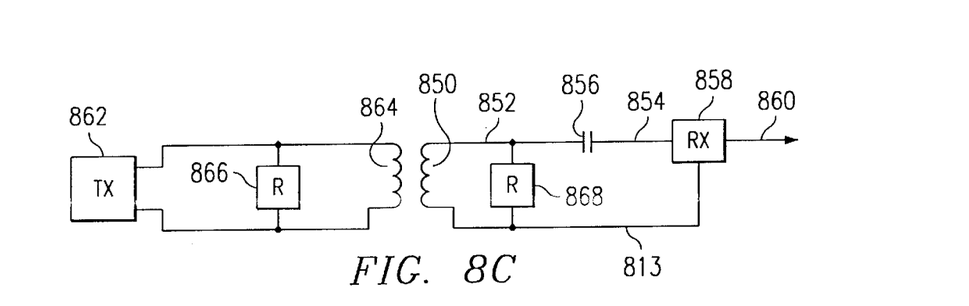

Referring now to FIGS. 8A–C, there are illustrated alternate embodiments for the transmit/receive operation on the transponder 400. In FIG. 8A, there is provided an oscillator 800 which drives an external inductive element 802. Typically, there is some type of load 804 disposed across the inductive element 802. This is the primary power that is provided to the system. A separate inductive element 806 is provided on the transponder 400, for being inductively coupled to the inductive element 802. Thereafter, a voltage is generated across the inductive element 806, the inductive element 806 being connected between nodes 808 and 810. A diode 812 is connected between node 808 and a power node 814, and a power supply capacitor 816 is disposed across node 814 and a node 810. This allows the voltage on node 808 to be rectified with diode 812.

In the alternative embodiment of FIG. 8B, the receive operation utilizes a separate inductive element or antenna 824 in the transponder 400, which is operable to be connected between nodes 809 and 811. Node 809 is capacitively coupled to a transmit node 830 with a capacitor 832, the capacitor 832 being a coupling capacitor. A transmitter 834 is provided for transmitting received data from a line 836 to the node 830, which is then coupled to the node 809 to impress the RF signal across the inductive element 824.

A corresponding inductive element 840 is disposed on the external control system 110, which inductive element 840 is operable to be disposed proximate to the inductive element 824, but external to the human body. The inductive element 840 is basically a "pick-up" element which is operable to receive information and function as an antenna, and provide the received signal to a receiver 842. The structure of FIG. 8B is a separate structure, such that node 809 is isolated from node 808, the power receiving node. However, it should be understood that any harmonics of the oscillator 800 would, of course, leak over into the inductive element 824. This can be tuned out with the use of some type of tuning element 844 on the transponder 400 disposed across inductive element 824, and also a tuning element 846 disposed across the inductive element 840, i.e., the antenna.

Referring now to FIG. 8C, there is illustrated a simplified schematic diagram of the receive portion. The transponder 400 has associated therewith a separate receive antenna or inductive element 850 disposed between node 813 and a node 852. Node 852 is capacitively coupled to a receive node 854 with a coupling capacitor 856. A receiver 858 is provided for receiving the information transmitted thereto and providing on the output thereof data on a data line 860. The receiver 858 is operable to receive the RF signal, demodulate the data therefrom, and provide digital data on the output 860. External to the human body and the transponder 400 is a transmitter 862 which is operable to impress a signal across an external inductive element 864. The inductive element 864 basically provides the RF energy and is essentially tuned with a tuning element 866. A corresponding tuning element 868 is provided on the transponder 400 and disposed across inductive element 850, the inductive element 850 acting as an antenna, as well as the inductive element 864.

Note that in circumstances where the signals of the transponder 400 cannot be adequately received therefrom and/or power coupled thereto, selected portions of all of the external control system 110 may need to be inserted into the body proximate to the transponder 400 in order to couple the transmit/receive signals and power. Furthermore, where more than transponder 400 is used, communication of power and data signals between the various transponders 400 may need to employ distinct time periods (i.e., time multiplexing) when communication occurs using a single common frequency, or discrimination circuits may need to be used where communication occurs simultaneously with the plurality of implanted transponders 400 having different oscillator frequencies.

Figure 9:
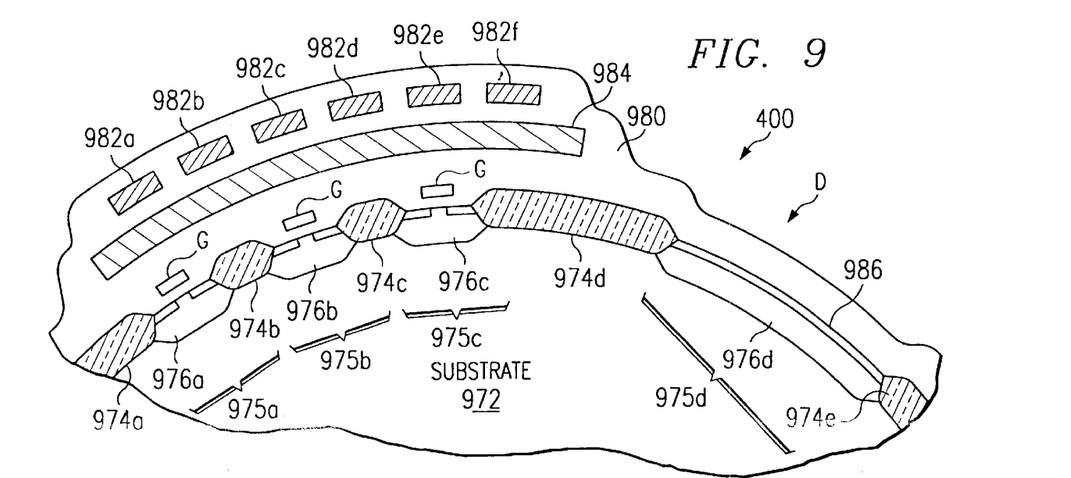
FIG. 9 illustrates a cross section of the outer semiconductor shell of a transponder, in accordance with a disclosed embodiment.

Referring now to FIG. 9, there is illustrated a cross section of the outer semiconductor shell of a transponder 400, in accordance with a disclosed embodiment. The transponder 400 includes a spherical semiconductor substrate 972 fabricated in accordance with techniques described in the above-referenced U.S. Patent application entitled "Spherical Shaped Semiconductor Integrated Circuit." The substrate 972 is of one conductivity type, such as n-type, which can be fabricated from phosphorous-doped silicon. Thick field oxide layers 974a, 974b, 974c, 974d and 974e are formed on the surface of the substrate 972 at discreet locations to define separate active areas 975a, 975b, 975c, and 975d therebetween. The active areas (975a, 975b, 975c, and 975d) may include p-type wells 976a, 976b, 976c and 976d. Within the wells 976a, 976b and 976c are formed NMOS transistors with polysilicon gates G. The gates G are embedded in a lower portion of a multi-level dielectric layer 980. Individual windings 982a, 982b, 982c, 982d, 982e and 982f are shown embedded in an upper portion of the dielectric layer 980. The individual windings (982a, 982b, 982c, 982d, 982e and 982f) may be portions of separate coils 406 used for different purposes. For example, windings 982a and 982b can be used for coupling RF power to the transponder 400. Windings 982c and 982d can be used as a receiving antenna for RF data input, and windings 982e and 982f can be used as a radiating antenna for RF data output. Preferably, a ferromagnetic layer 984 is disposed beneath the coil windings (982a, 982b, 982c, 982d, 982e and 982f) to enhance current induction during the power and signal coupling phases. An n-type layer 986 is formed at the surface of the substrate 972 between field oxide portions 974d and 974e. The n-type layer 986 together with the underlying p-type layer 976d define one of the diodes D.

It will be appreciated that the reverse leakage current of the diodes D is affected by the radiation experienced by the transponder 400. This phenomenon is described in the Rikner et al. article referred to hereinabove. The radiation to which the transponder 400 is exposed creates lattice defects in the monocrystalline silicon in the vicinity of the PN junction between p-type region 976d and n-type region 986.

These defects are permanent so that the radiation has a cumulative effect on the reverse leakage current of each of the diodes D. The diodes D, connected in parallel, define a dosimeter whose output is defined at node 764 of the circuit of FIG. 7. The voltage at node 764 increases cumulatively with the radiation dosage applied to the tumor 234 over a series of procedures. The CPU 114 records the dosage levels and data corresponding to the voltage level on node 764 during each procedure so that calibration points can be established from one procedure to the next for a particular patient.

It will be appreciated that the radiation also has an impact on the active circuits of the transponder 400, such as the transistors located in active areas 975a, 975b and 975c. These active areas (975a, 975b, and 975c) are covered by the ferromagnetic layer 984 and the coils 982a–982f, thus protecting to some degree the active circuitry of the transponder 400 from the radiation to which the transponder 400 is exposed during treatment. This permits the transponder 400 to continue to function properly even though it ultimately will be rendered useless after a series of radiation treatments.

Figure 10:
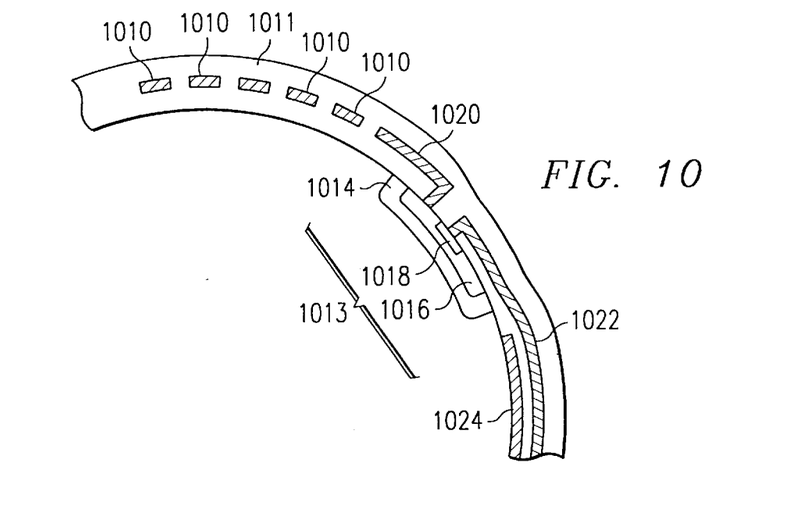
FIG. 10 illustrates a cross-sectional diagram of the surface of the ball IC illustrating the conductive strips forming the inductive element.

Referring now to FIG. 10, there is illustrated a cross-sectional diagram of the surface of the transponder 400 illustrating the conductive strips forming the inductive element 604. The conductive strips are referred to by reference numeral 1010 which are spaced above the surface of the integrated circuit of the transponder 400 by a predetermined distance, and separated therefrom by a layer of silicon dioxide. A passivation layer 1011 is then disposed over the upper surface of the conductive strips 1010. The conductive strips 1010 can be fabricated from polycrystalline silicon but, it would be preferable to form them from the upper metal layer to result in a higher conductivity strip. This will allow the strips 1010 to be narrower and separated from each other by a larger distance. This separation would reduce the amount of capacitance therebetween.

One end of the strips 1010 is connected to a diode structure 1013. The diode structure 1013 is formed of an N-well implant region 1014 into which a P-well implant region 1016 is disposed, and an N-well implant region 1018 disposed within the P-well implant region 1016. This forms a PN diode where one end of the conductive strips 1010, a conductive connection 1020, is connected to the P-well 1016 implant region, and a conductive layer 1022 is connected at one end to the N-well implant region 1018. This conductive layer or strip 1022 extends outward to other circuitry on the integrated circuit and can actually form the large storage capacitor 620. Since it needs to go to a capacitor directly, a lower plate 1024 formed of a layer of polycrystalline silicon or metal in a double-metal process, could be provided separated therefrom by a layer of oxide.

Figure 11:
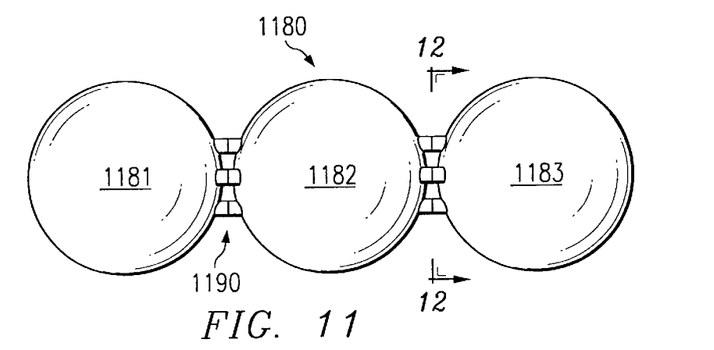
FIG. 11 illustrates a side elevation of a cluster of three semiconductor balls that may be employed in a cooperative function.

Referring now to FIG. 11, there is illustrated a side elevation of a cluster 1180 of three semiconductor transponder balls that may be employed in a cooperative function. Although a single transponder 400 can include the foregoing functions, more complex monitoring functions with multiple transducers can be implemented using multiple ball systems used in injection and implant procedures, and attached to prosthetics, catheters, needles and other medical-related apparatus. For example, transponder 1181 (similar to transponders 236, 238, and 400) can include power receiving and data transmission functions, and radiation dosimetry functions. Alternatively, the transponder's 1081 sole function can be dedicated to that of a miniature ball-shaped battery. Transponder 1182 can include a first transducer function, such as pressure sensing, and transponder 1183 can include a second transducer function, such as measuring strain, pH, $pO^2$, $pCO_2$, or temperature, as the particular application requires. Connections between the balls are made through metal contacts 1190, which may be solder bumps, and as described in greater detail hereinbelow, the metal contacts 1190 may be used for a variety interface functions, such as power, data, and a signal bypass path.

Figure 12:
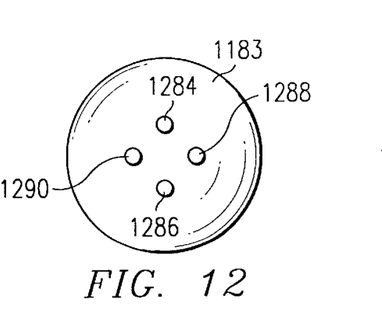
FIG. 12 illustrates a cross section taken through the line 11—11 of FIG. 11.

Referring now to FIG. 12, there is illustrated a cross section taken along the line 11—11 of FIG. 11. As mentioned hereinabove, the contacts 1190 may be employed to interface a variety of functions. For example, the contacts 1284 and 1286 of transponder 1183 may be power contacts, such as a positive 3.0 volts and ground, which can be passed from transponder 1181 (if transponder 1181 were to provide the power function for the cluster 1180) to transponder 1182, and then around transponder 1182 to transponder 1183 by conductors on the surface of transponder 1182 using two of a group of similar contacts of contacts 1190 to power transponder 1183. The contacts 1288 and 1290 may be data and control contacts for communications between balls of the cluster 1180. Similar data and control contacts may exist among contact group 1190 between transponder 1182 and transponder 1183 to the extent needed.

Figure 13:
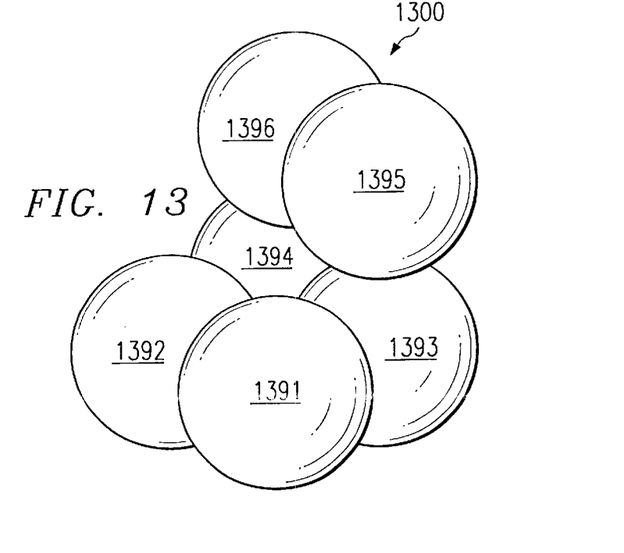
FIG. 13 illustrates a 3-D ball cluster in a cooperative orientation.

Referring now to FIG. 13, there is illustrated a 3-D ball cluster in a cooperative orientation. As an example of the versatility of such ball systems is illustrated where the cluster 1300 specifically shows six balls 1391, 1392, 1393, 1394, 1395 and 1396 (all similar to transponder 400), arranged in a three-dimensional configuration. It will be appreciated that various other cluster arrangements are possible which have fewer balls, and are limited only by the constraints of the end-use application. Each of the balls 1391, 1392, 1393, 1394, 1395 and 1396 of the cluster 1300 can perform different electronic functions, and communicate with each other through contacts (not shown here, but discussed in detail in FIGS. 11 and 12). Such cluster arrangements can provide a mix of, for example, three battery balls 1181, 1182, and 1183, which provide ample power for the remaining energy-consuming balls, according to the functions provided. Such a mix may be necessary where a heating application is required for, for example, tumor ablation, or for more precise heating applications related to cartilage or ligament treatment.

Figure 14A:
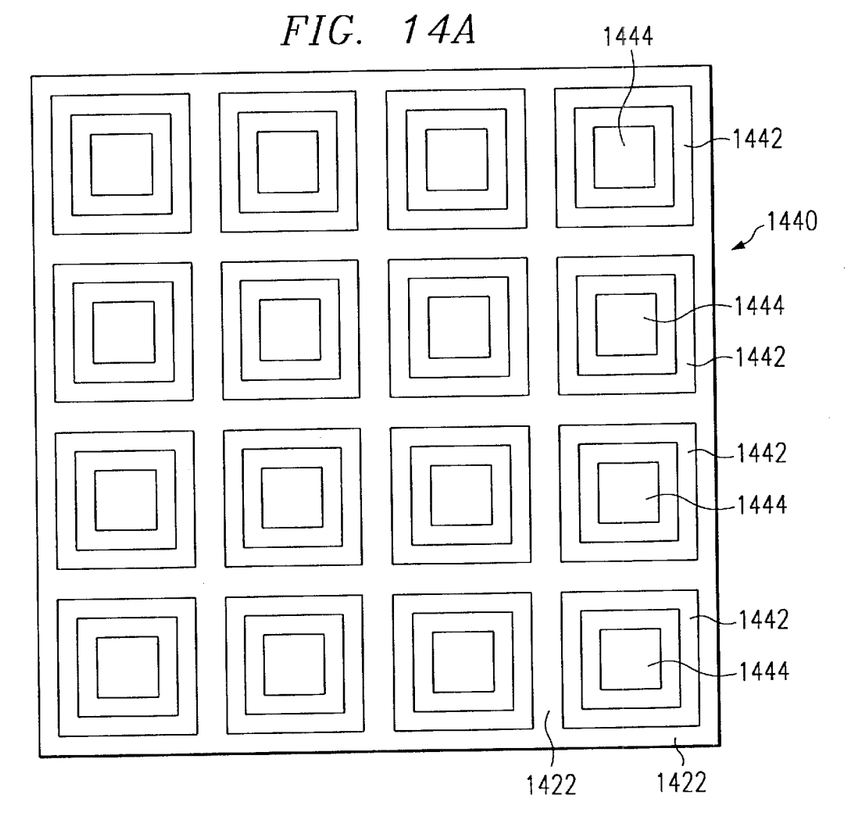
FIG. 14A illustrates a two-dimensional ionizing radiation detector structure adaptable to the disclosed semiconductor ball.

Referring now to FIG. 14A, there is illustrated a two-dimensional ionizing radiation detector structure adaptable to the disclosed semiconductor ball. Such a conventional two-dimensional detector array is disclosed in U.S. Pat. No. 5,627,377 by Hamilton, Jr., et al., entitled "Single Carrier-Type Solid-State Radiation Detector Device," issued on May 6, 1997. The detector can be fabricated on a single substrate of CdZnTe with various contact, grid, and signal layers grown by any of the following methods: molecular beam epitaxy, vapor phase epitaxy, metal-organic chemical vapor deposition over the substrate. In this two-dimensional array 1440, a plurality of mesa structures 1442 complete the array 1440 in a grid metalization layer 1422. The mesa structures 1442 are topped off with bumps 1444 for interfacing to external circuitry (not shown), where desired.

Figure 14B:
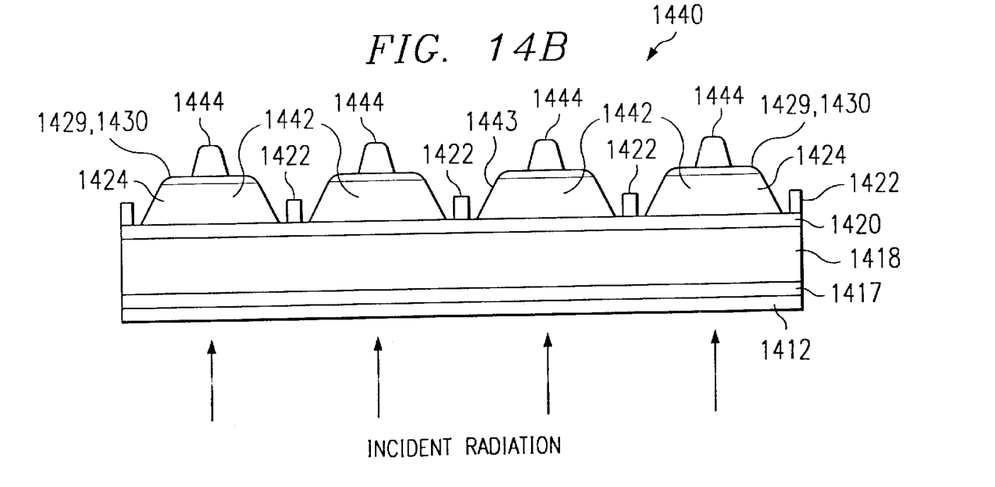
FIG. 14B illustrates the device structure for such an array of FIG. 14A

Referring now to FIG. 14B, there is illustrated the device structure for such an array of FIG. 14A. Incident radiation first strikes a cathode metalization layer 1412 over which a P-type contact layer 1417 is fabricated. Radiation is absorbed in a relatively thick detecting layer 1418. As disclosed, the detecting layer 1418 may range from 100 $\mu$m to at least 10,000 μm with typical values in the range of 1000–2000 μm. Overlying the detecting layer 1418 is a grid layer 1420 of P-type semiconductor conductor material. A passivation layer 1443 is then fabricated on the grid layer 1420 with a grid metalization 1422 layer formed thereafter on the passivation layer 1443, and contacts the grid layer 1420 through suitably formed apertures within the passivation layer 1443. The signal layer 1424 and overlying contact layer 1429 (and anode contact 1430) are differentiated into the plurality of mesa structures 1442. As mentioned hereinabove, interface bumps 1444, which can be made from In, are fabricated on the anode structure 1430 for contact purposes.

Although the preferred embodiment has been described in detail, it should be understood that various changes, substitutions and alterations can be made therein without departing from the spirit and scope of the invention as defined by the appended claims.

What is claimed is:

1. A system for detecting a dosage of radiation received by a tumor during radiation treatment, comprising:
   a radiation source that is adapted to be directed at the tumor;
   a central processing unit connected to the radiation source for monitoring and controlling the radiation treatment; and
   one or more dosimetry transponders adapted to be injected into the tumor, each said dosimetry transponder having,
      a memory in which a unique identification code is stored for distinguishing each transponder from the other transponders,
      a communication circuit for communicating power and control signals between said transponder and said central processing unit, and
      one or more detectors for detecting radiation and converting the detected radiation to a data signal.

2. The system of claim 1, wherein each said dosimetry transponder comprises a spherical-shaped semiconductor substrate on which circuitry is formed.

3. The system of claim 1, further comprising a catheter delivery system that is adapted for injecting a slurry of multiple said dosimetry transponders into the tumor via a feeding blood vessel.

4. The system of claim 1, further comprising first and second receivers located in a spaced relationship to each other and connected to said central processing unit for detecting the precise position of each of the dosimetry transponders are adapted to be injected into the tumor to permit three-dimensional mapping of locations of said transponders for display during the radiation treatment.

5. The system of claim 1, wherein said central processing unit connects to a display for presenting dosimetry data.

6. The system of claim 1, wherein said one or more transponders comprise radiation-sensitive diodes for detecting radiation interspersed among one or more communication coils for communicating power and data signals to said one or more transponders.

7. A method for detecting a dosage of radiation received by a tumor during radiation treatment, comprising the steps of:
   directing a radiation source at the tumor;
   connecting a central processing unit to the radiation source for monitoring and controlling the radiation treatment; and
   injecting one or more dosimetry transponders into the tumor, each dosimetry transponder having,
      a memory in which a unique identification code is stored for distinguishing each transponder from the other transponders,
      a communication circuit for communicating power and control signals between the transponder and the central processing unit, and
      one or more detectors for detecting radiation and converting the detected radiation to a data signal.

8. The method of claim 7, wherein each the dosimetry transponder in the step of injecting comprises a spherical-shaped semiconductor substrate on which circuitry is formed.

9. The method of claim 7, further comprising a catheter delivery system in the step of injecting for injecting a slurry of multiple the dosimetry transponders into the tumor via a feeding blood vessel.

10. The method of claim 7, further comprising first and second receivers in the step of connecting located in a space relationship to each other and connected to the central processing unit for detecting the precise position of each the dosimetry transponder injected into the tumor to permit three-dimensional mapping of locations of the transponders for display during the radiation treatment.

11. The method of claim 7, wherein the central processing unit in the step of connecting connects to a display for presenting dosimetry data.

12. The method of claim 7, wherein the one or more transponders in the step of injecting comprise radiation-sensitive diodes for detecting radiation interspersed among one or more communication coils for communicating power and data signals to the one or more transponders.

13. A system for detecting a dosage of radiation received by a tumor during radiation treatment, comprising:
   a radiation source that is adapted to be directed at the tumor;
   a central processing unit connected to the radiation source for monitoring and controlling the radiation treatment; and
   one or more dosimetry transponders are adapted to be injected into the tumor, each said dosimetry transponder having,
      a communication circuit for communicating power and control signals between said transponder and said central processing unit, and
      one or more detectors for detecting radiation and converting the detected radiation to a data signal,
   wherein the system further comprises first and second receivers located in a spaced relationship to each other and connected to said central processing unit for detecting the precise position of each of the dosimetry transponder adapted to be injected into the tumor to permit three-dimensional mapping of locations of said transponders for display during the radiation treatment.

14. The system of claim 13, wherein each said dosimetry transponder comprises a spherical-shaped semiconductor substrate on which circuitry is formed.

15. The system of claim 13, further comprising a catheter delivery system that is adapted for injecting a slurry of multiple said dosimetry transponders into the tumor via a feeding blood vessel.

16. The system of claim 13, wherein each said dosimetry transponder includes a memory in which a unique identification code is stored for distinguishing one said transponder from another said transponder.

17. The system of claim 13, wherein said central processing unit connects to a display for presenting dosimetry data.

18. The system of claim 13, wherein said one or more transponders comprise radiation-sensitive diodes for detecting radiation interspersed among one or more communication coils for communicating power and data signals to said one or more transponders.

19. A method for detecting a dosage of radiation received by a tumor during radiation treatment, comprising the steps of:

directing a radiation source at the tumor;

connecting a central processing unit and first and second receivers to the radiation source for monitoring and controlling the radiation treatment, the receivers being located in a spaced relationship to each other, the radiation source and the tumor for detecting the precise position of each of the dosimetry transponders injected into the tumor to permit three-dimensional mapping of locations of the transponders for display during the radiation treatment; and injecting one or more dosimetry transponders into the tumor, each dosimetry transponder having,
a communication circuit for communicating power and control signals between the transponder and the central processing unit, and
one or more detectors for detecting radiation and converting the detected radiation to a data signal.

20. The method of claim 19, wherein each the dosimetry transponder in the step of injecting comprises a spherical-shaped semiconductor substrate on which circuitry is formed.

21. The method of claim 19, further comprising a catheter delivery system in the step of injecting for injecting a slurry of multiple dosimetry transponders into the tumor via a feeding blood vessel.

22. The method of claim 19, wherein each of the dosimetry transponders in the step of injecting includes a memory in which a unique identification code is stored for distinguishing each transponder from the other transponders.

23. The method of claim 19, wherein the central processing unit in the step of connecting connects to a display for presenting dosimetry data.

24. The method of claim 19, wherein the one or more transponders in the step of injecting comprise radiation-sensitive diodes for detecting radiation interspersed among one or more communication coils for communicating power and data signals to the one or more transponders.

* * * * *